United States Patent [19]
La Chappelle-Reynolds

[11] Patent Number: 5,899,206
[45] Date of Patent: May 4, 1999

[54] TANNING BED FACE SHIELD

[76] Inventor: Charmaine M. La Chappelle-Reynolds, 18904 N. Day Mt. Spokane, Mead, Wash. 99021

[21] Appl. No.: 08/740,231

[22] Filed: Oct. 25, 1996

[51] Int. Cl.$^6$ ........................................................ A61F 5/37
[52] U.S. Cl. ............................................ 128/846; 128/857
[58] Field of Search ..................................... 128/845, 846, 128/857, 858; 607/91; 2/2; 135/139

[56] References Cited

U.S. PATENT DOCUMENTS

| | | | |
|---|---|---|---|
| 1,051,349 | 1/1913 | Neitro | 607/91 |
| 3,741,218 | 6/1973 | Novak | 607/91 |
| 4,550,713 | 11/1985 | Hyman | 128/849 |
| 4,660,561 | 4/1987 | Nielsen | 607/91 |

*Primary Examiner*—Michael A. Brown
*Attorney, Agent, or Firm*—Wells, St. John, Roberts, Gregory & Matkin P.S.

[57] ABSTRACT

A tanning bed face shield is described, including a light shielding body having an anterior surface and opposed side surfaces adjoining the anterior surface. The anterior and side surfaces extend axially between a superior and an inferior end of the light shielding body. The surfaces fold to form a head receiving compartment sized to loosely receive and cover a user's face with an air space between the face and the folded surfaces. A flange assembly at the inferior end of the light shielding body is also folded with the other surfaces to a position substantially normal to the surfaces and partially spanning the inferior end. The flange assembly defines a substantially inverted U-shaped recess configured to loosely receive a user's chin and neck.

16 Claims, 14 Drawing Sheets

TANNING BED FACE SHIELD

TECHNICAL FIELD

The present invention relates to shields for guarding the face against harmful rays and more particularly to such a shield that may be used in conjunction with tanning beds.

BACKGROUND OF THE INVENTION

Tanning beds are presently used to darken skin as a safer, more effective alternative to sun bathing. Modern tanning beds incorporate light sources that make use of radiation that is minimally harmful to the skin, yet more effective for quickly altering skin pigmentation. Still, however, such rays are harmful to the eyes, and users must wear eye protection to avoid potentially serious retinal damage.

Even with modern specially engineered light sources that are intended to be less harmful to skin, frequent tanning bed users will often cover their entire face to avoid inevitable wrinkling of facial skin. The most common used device to cover the face is a towel. Unfortunately, towels do not consistently cover all the desired areas, and do not promote normal breathing. Also, if the area directly under the chin is not carefully and skillfully covered, an embarrassing tan line will result. A problem has thus remained to adequately cover the face against the tanning rays.

As a solution, some tanning bed manufacturers reduce or eliminate the number of tanning elements in the head areas of their tanning beds. This does reduce the most harmful effect from direct exposure, but indirect rays emanating from below the neck line still reach the facial area and do not completely eliminate the need for shielding.

The present invention can be used to effectively eliminate facial tanning, either in tanning beds or in natural surroundings, by providing a physical, preferably opaque shield that will effectively eliminate passage of tanning rays to the facial area, while permitting normal breathing. The present invention further provides for a consistent positionable shaded area adjacent the chin. Still further, the present invention provides the user with an easily portable screen configuration that may be folded between a flattened storage and transport condition, and an open operative configuration.

BRIEF DESCRIPTION OF THE DRAWINGS

Preferred embodiments of the invention are described below with reference to the following accompanying drawings.

FIG. 10 is a perspective view of another alternate shield in its operative configuration;

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Several exemplary forms of the present tanning bed face shield are commonly designated in the drawings by the reference numeral 10. In any of the illustrated forms, the face shield 10 is intended primarily for use in a conventional tanning bed 11, to shield a user's head (particularly the facial and temporal surfaces) from the tanning light rays produced within the tanning bed 11. It is noted that the forms illustrated and described below are examples of the present invention and that other forms and configurations may also be envisioned that fall within the scope of the claims following this description.

In all the forms illustrated, a light shielding body 15 is shown, including an anterior surface 17, and opposed side surfaces 19, 21 adjoining the anterior surface 17. The preferred anterior and side surfaces 19, 21 extend axially between a superior end 23 and a inferior end 25 of said light shielding body 15.

Figure 5:
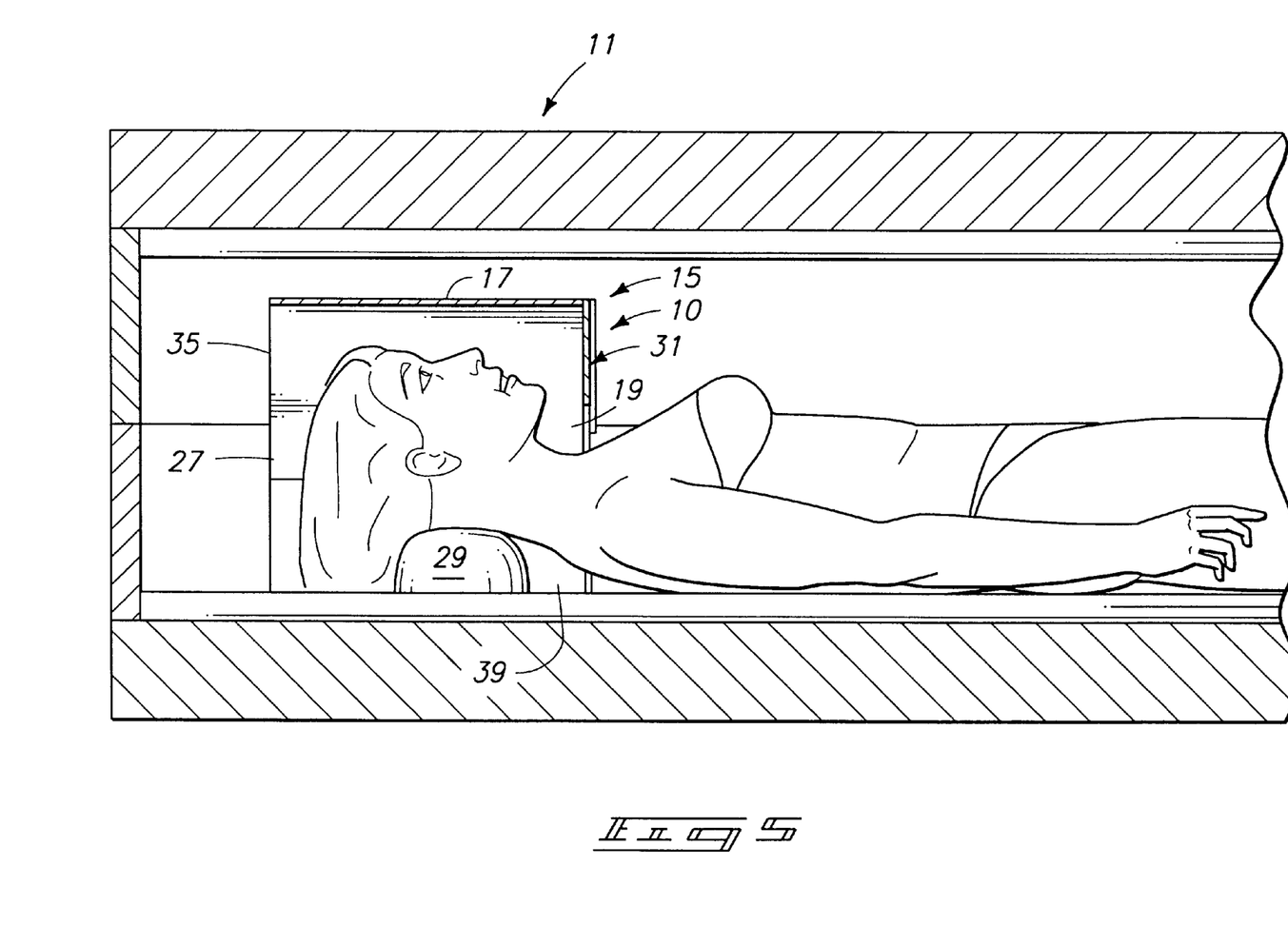
FIG. 5 is a diagrammatic fragmented view showing placement of another preferred form of the present shield over a user's face in a tanning bed, the shield being shown graphically and sectioned substantially along the user's mid-sagittal plane.
Figure 18:
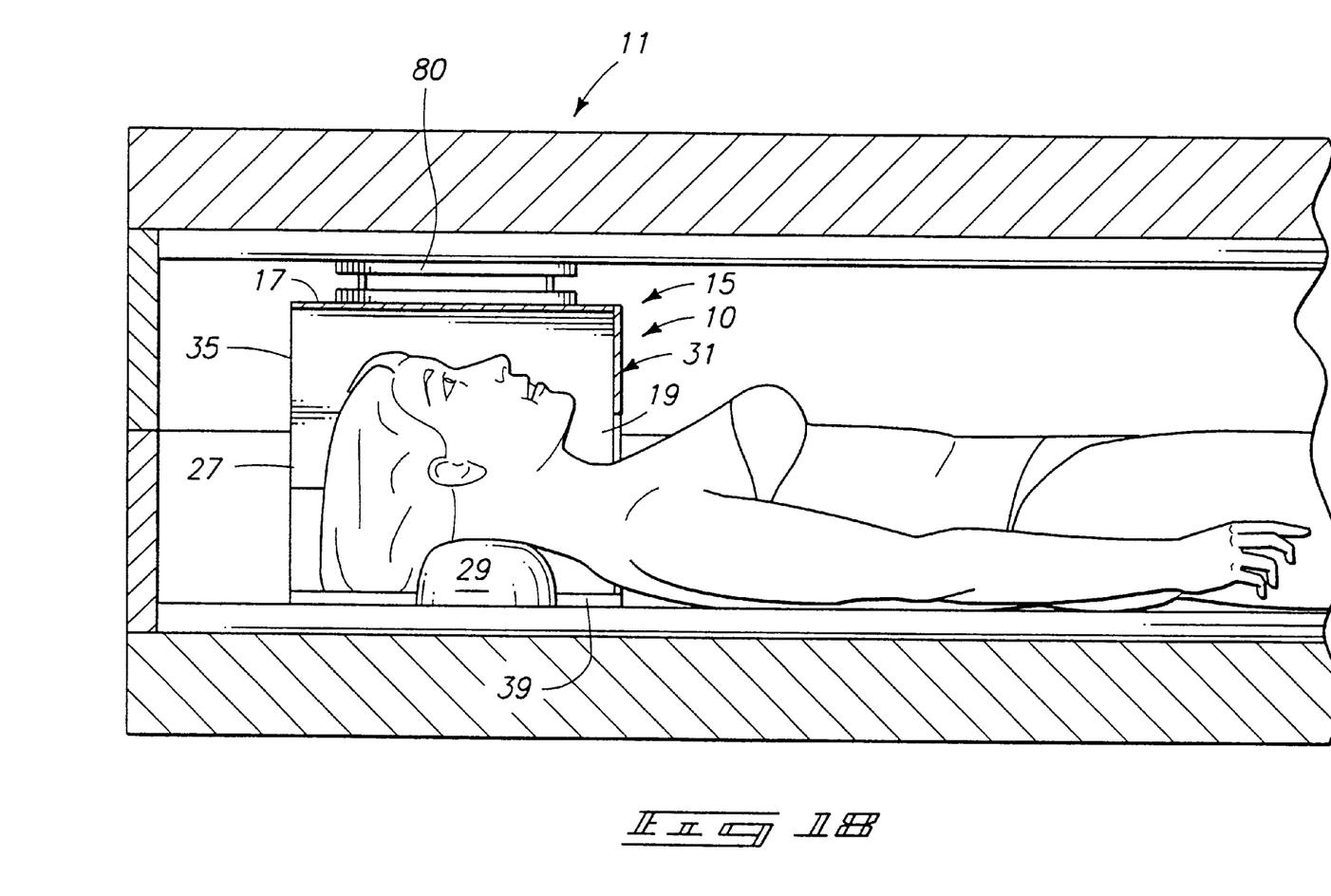
FIG. 18 is a view of a form of the present shield that is mounted directly to the tanning bed.

The surfaces 17, 19, and 21 form a head receiving compartment 27 that is sized to loosely receive and cover a user's face with an air space between the face and the named surfaces. The air space is of sufficient size, as shown in FIGS. 5 and 18, to allow ventilation within the compartment 27 and some freedom of movement of the user's head while resting against a pillow 29 that is typically provided within the tanning bed 11.

In all examples shown, a flange 31 is provided at the inferior end of the light shielding body, formed along a plane that is substantially normal to the surfaces 17, 19, and 21, partially spanning the inferior end 25 and the head receiving compartment 27.

Figure 1:
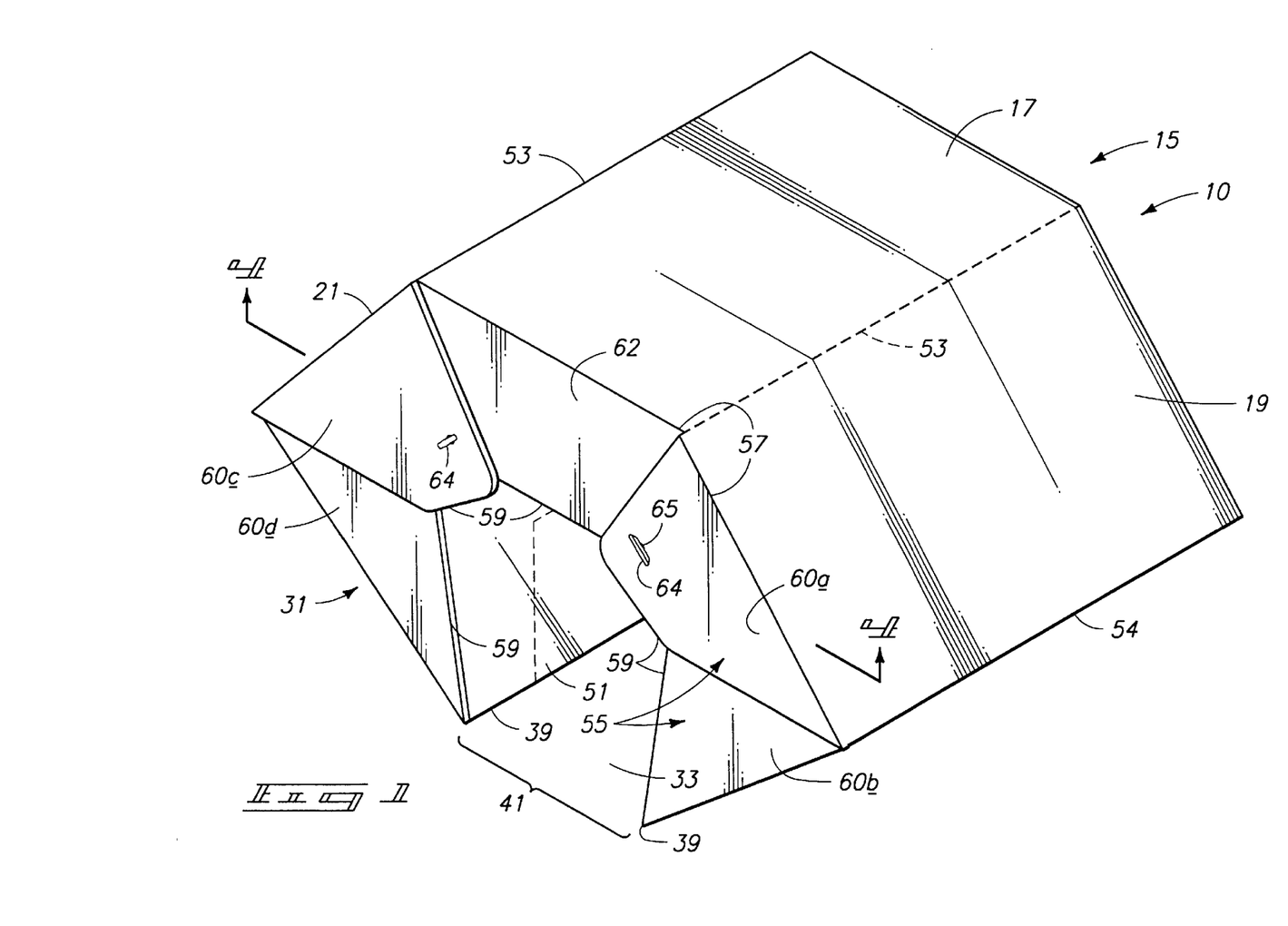
FIG. 1 is a perspective view of a first preferred form of the present shield in an open, operative condition.
Figure 6:
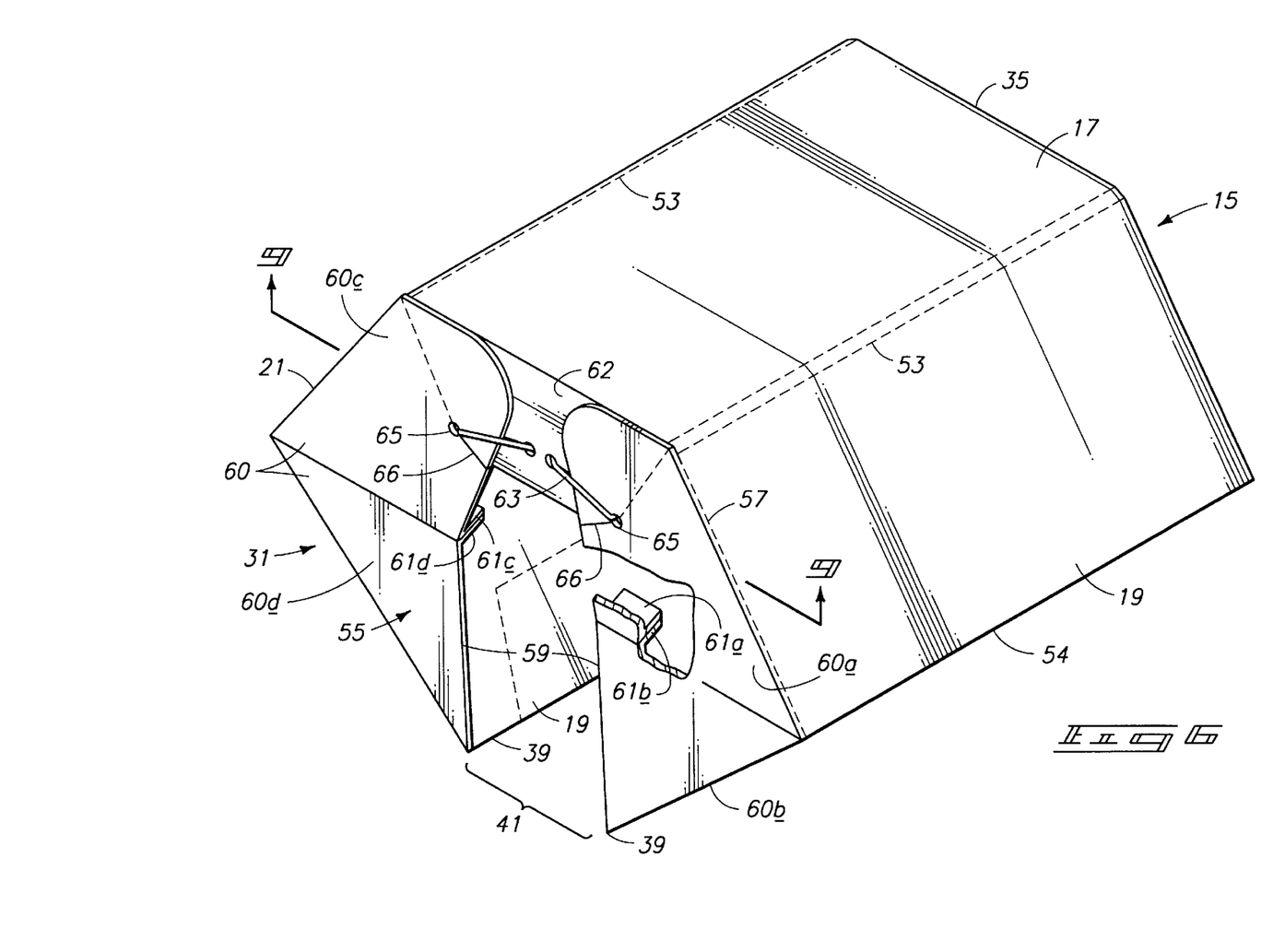
FIG. 6 is a perspective view of an alternate preferred form of the present shield in an open, operative condition.

In the operative condition of each preferred form, the flange 31 defines a substantially inverted U-shaped recess 33 configured to loosely receive a user's chin and neck, substantially as shown in FIGS. 1, 6 and 10. In use, the flange 31 extends to or just past the point of the user's chin (in a posterior direction toward the neck) to shield the facial and temporal surfaces against tanning radiation emanating from below the chin line.

In the illustrated examples, the superior ends 23 include lateral superior end edge surfaces 35 defining superior openings 37. The openings 37 permit ventilation through the length of the shield. Also, it has been found that little if any tanning rays will enter the head receiving compartment 27 in this area. It has further been found that production and cost of the shield 10 is minimized by leaving the superior end 23 open substantially as shown. Folding of the shields between the inoperative and operative conditions is also made easier and faster by leaving the superior end 23 open.

The side surfaces 19, 21 terminate at spaced apart axial posterior support edges 39 that define an axial posterior head receiving opening 41 adjoining the inverted U-shaped recess and, in the preferred forms, the superior opening 37 (FIG. 1). Thus the shield includes openings at the superior (at the crown of the head), inferior (at the chin), and posterior (at the back side of the head) sides thereof.

In preferred forms, the shield further includes a removable cut-out section 49, 51 on each of the respective side surfaces 19, 21 for receiving a tanning bed pillow 29, typically provided in many conventional forms of tanning beds 11 The cut-out sections 49, 51 are removable, allowing the user the option to remove them so the pillow 29 that is typically found in tanning beds (FIG. 5) may be received across the shield. Otherwise the sections may be left in place should the user wish to use the shield in, say, an outdoor environment or in tanning beds where no pillow is provided. The cut-out sections 49, 51 may be defined by perforated lines that will allow separation of the sections at the whim of the user.

In the presently preferred forms, the surfaces 17, 19, 21, and flange 31 are all formed of a single sheet of foldable material. More specifically, the sheet is an opaque, foldable material such as corrugated sheet stock, of either plastic or paper. This has been found preferable to, say, plastic injection molded solid shields, since the foldable material will allow the user to fold the shield to a relatively flat configuration when it is not in use. Thus the shield can be easily transported and stored in a relatively small space.

In the exemplary forms of the invention, the surfaces 17, 19, and 21 are interconnected and fold along a plurality of axial or longitudinal pairs of fold lines 53, 54 (FIGS. 3, 6–8, 10 and 16) that are all preferably parallel and of the same approximate length. The central fold lines 53 adjoin the anterior surface 17 and enable the named surfaces to be folded from the flat sheet to form the head receiving compartment 27. The fold lines 54 adjoin the side surfaces to affect the shape of the compartment, to loosely receive and cover a user's face with an air space for ventilation between the face and said surfaces.

The flange assembly 31, differs in the preferred forms but, in general is made up of a number of individual flange sections, generally indicated at 55, that are joined to the anterior and side surfaces along lateral, preferably parallel flange fold lines 57. In the alternate versions shown in FIGS. 10–17 additional parallel fold lines 58 are provided at the inferior end 25 of the body 15. The flange fold lines enable the user to fold the various flange sections together, forming a completed flange 31 that partially spans the head receiving compartment 27 and forms the substantially inverted U-shaped recess 33 which is configured to loosely receive a user's chin and neck.

More specifically, each flange section folds to expose a flange edge 59 that folds with the associated flange sections about the flange fold lines 57 to define the inverted U shaped recess 33. In the alternate form shown in FIGS. 10–17, the fold lines 58 and flange edge 59 are coincidental.

It is noted that the flange sections differ in shape between embodiments. The different flange section shapes exemplify a variety of configurations, any of which may be folded to form the completed flanges 31 with recesses 33 as shown in FIGS. 1, 6 and 10.

Figure 7:
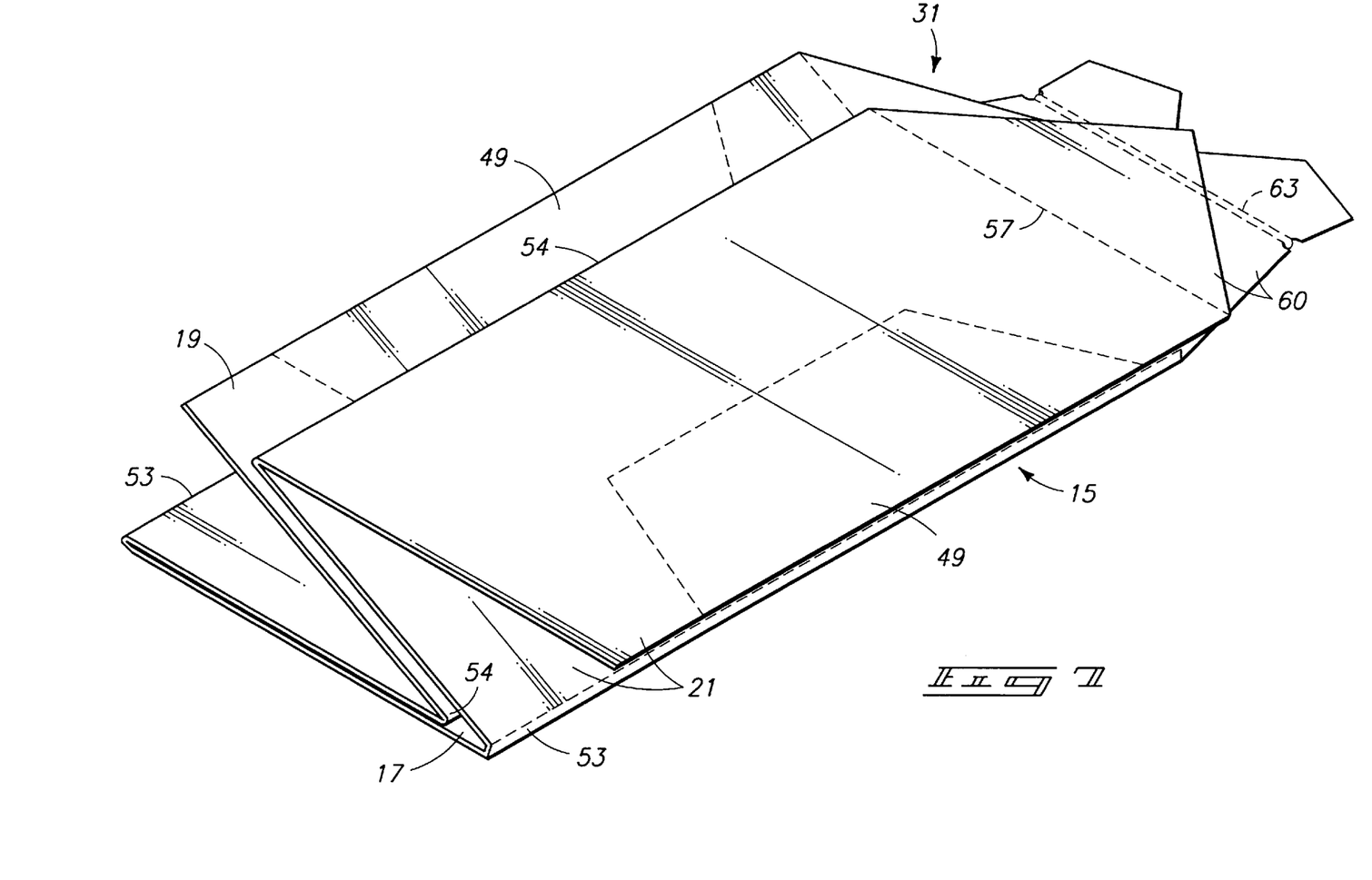
FIG. 7 is a perspective view of the alternate form in a folded inoperative condition.
Figure 8:
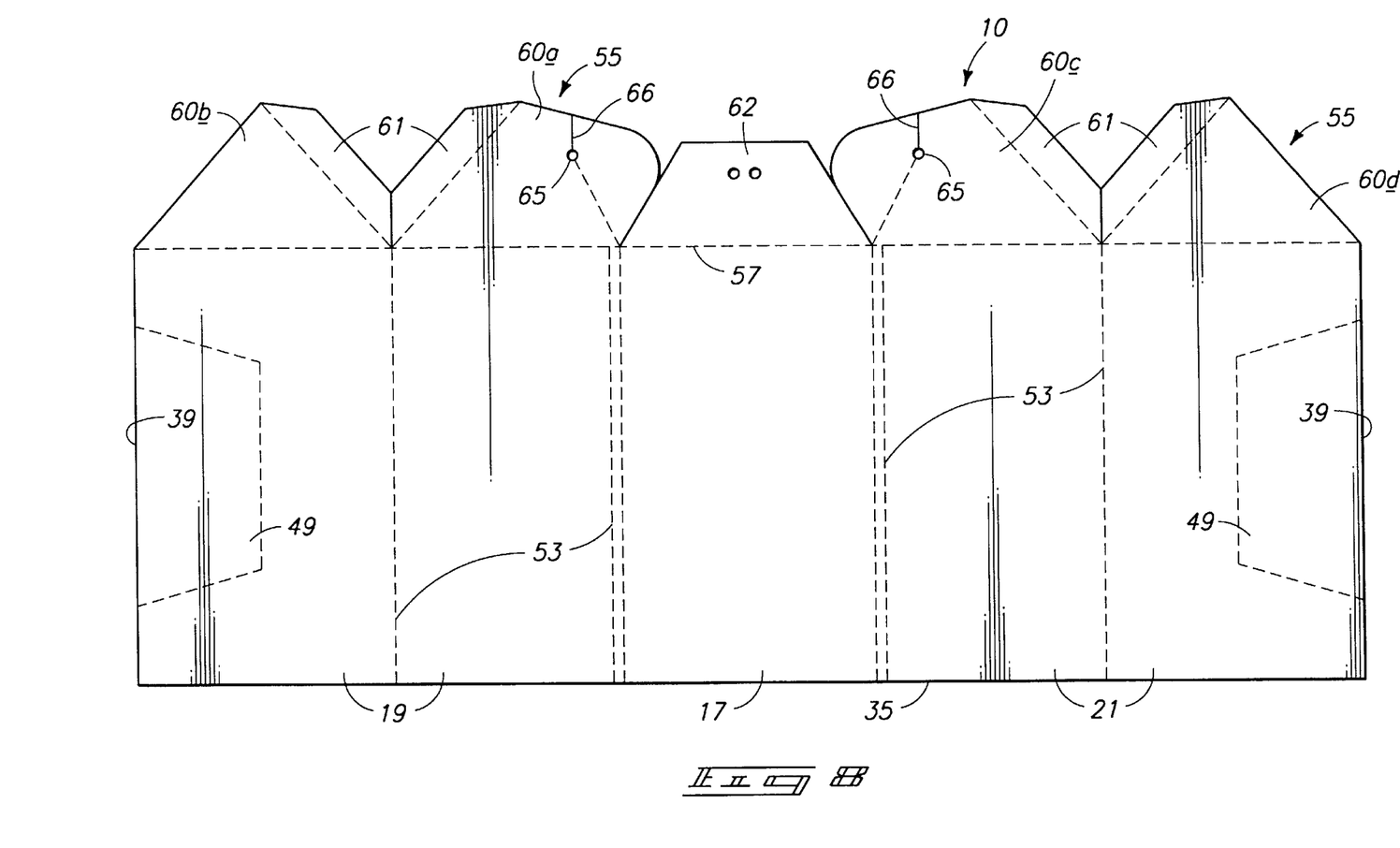
FIG. 8 is a flat pattern view of the alternate form.
Figure 9:
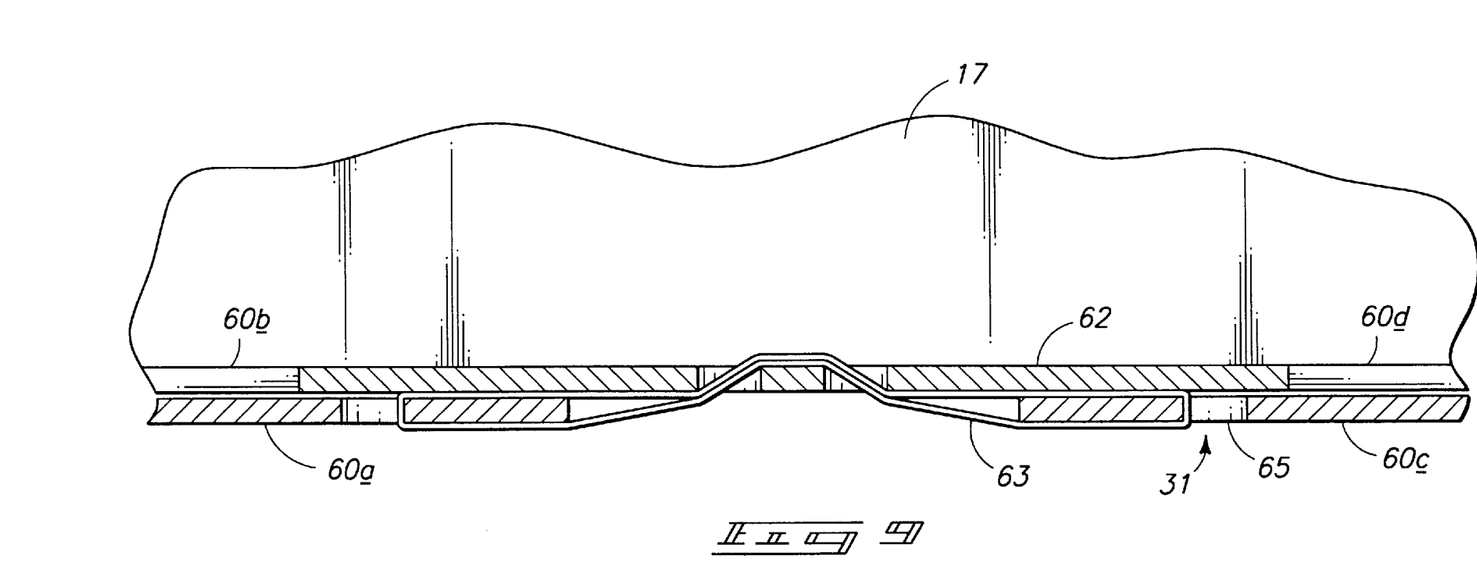
FIG. 9 is an enlarged fragmented sectional view taken substantially along line 9—9 in FIG. 6.
Figure 11:
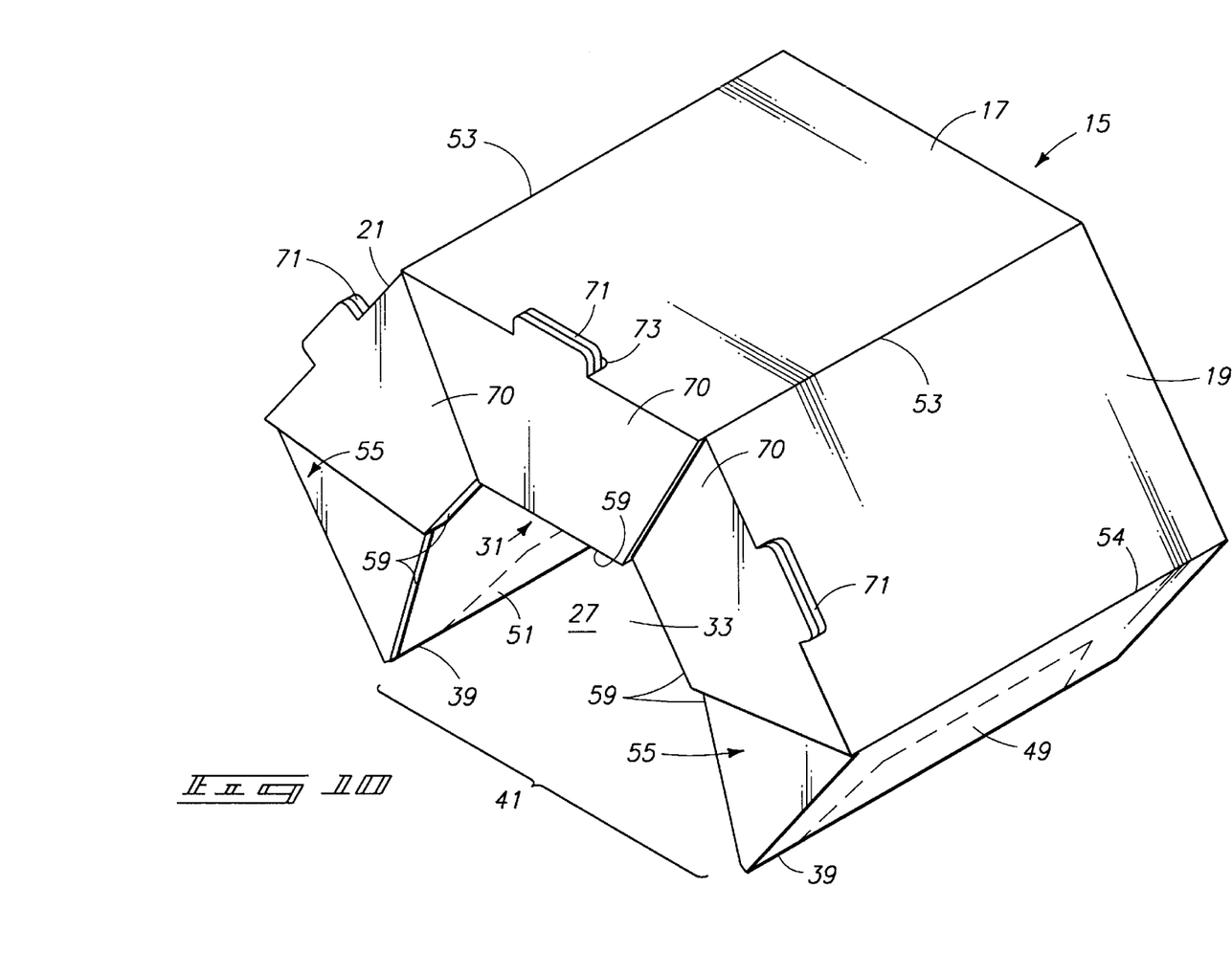
FIG. 11 is an anterior plan view of the form shown in FIG. 10.

In the first two preferred forms (FIGS. 1–5 and 6–10), several flange sections are individually numbered at 60a, b, c, and d. In the second alternate form the sections 60a–d (FIGS. 6–10) are provided with foldable tabs 61a, b, c, and d respectively. Adjacent pairs of the tabs 61a, b; and 61c, d are folded, preferably during manufacturing. The tabs of each pair are secured together by glue (or another appropriate fastener) as shown in FIG. 6 to initially form parts of the flange assembly 31 and assist subsequent folding of the assembly between the open condition (FIG. 6), and the closed condition (FIG. 7). The flange sections 60a–d join with a single anterior flange section 62 that folds on the lateral fold line 57 and is joined to the anterior surface 17 to complete the flange 31.

To simplify folding of the first two preferred forms between open and closed conditions, a biasing member is provided to normally pull the flange sections 60a–d toward one another. In the preferred forms, the biasing member is a common rubber filament 63, threaded through a number of holes 65 formed in the anterior flange section 62 and adjoining flange sections 60a–d. A common household rubber band is preferred as the elastic filament 63 in the second preferred form to ease replacement should the band eventually wear and break.

Figure 4:
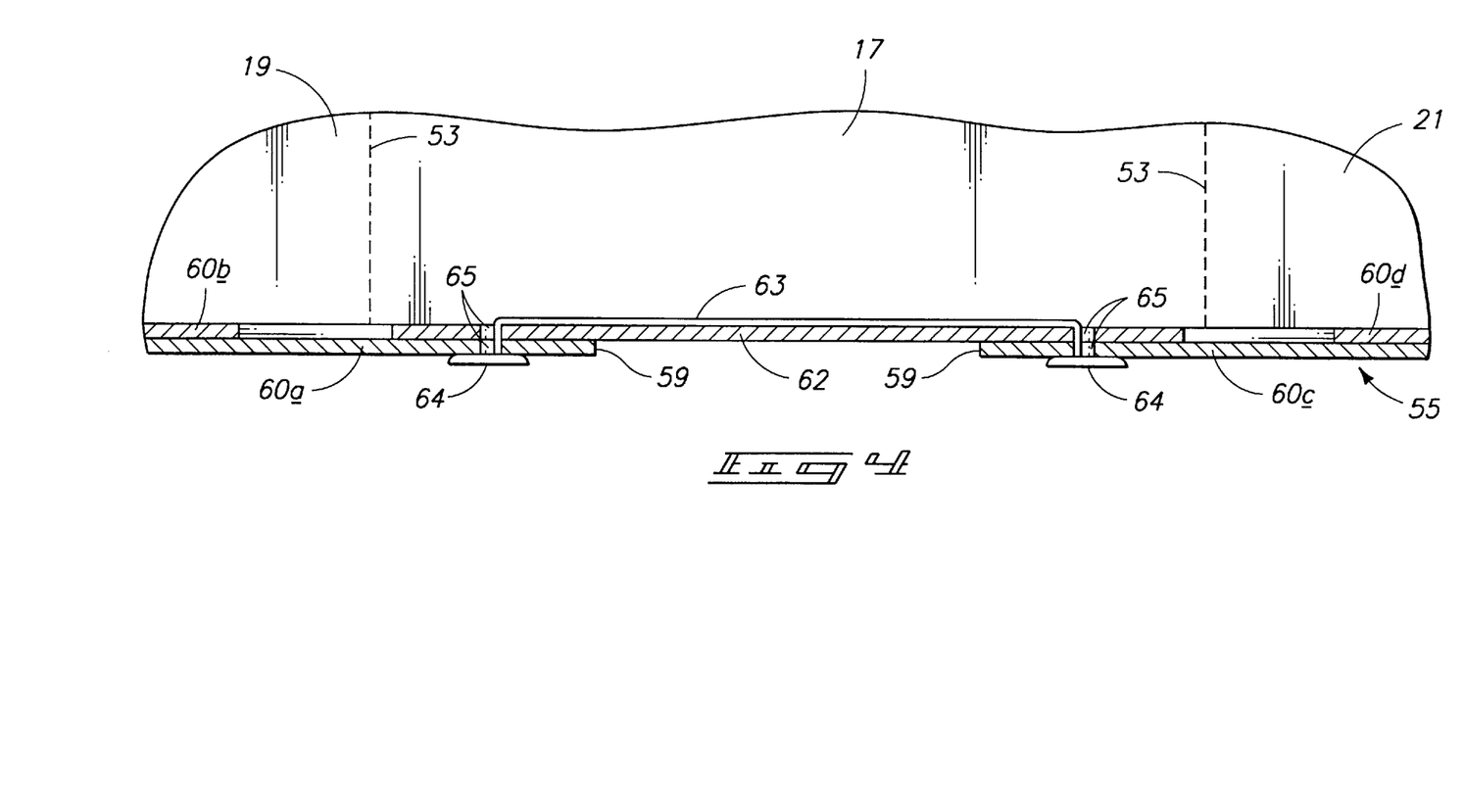
FIG. 4 is an enlarged fragmented sectional view taken substantially along line 4—4 in FIG. 1.

In the first preferred form, the filament is an elastic strip with conventional lock bars 64 at opposed ends. The bars 64 can be threaded through holes 65 and then tipped laterally as shown in FIG. 4, locking the ends of the filament in place.

Figure 2:
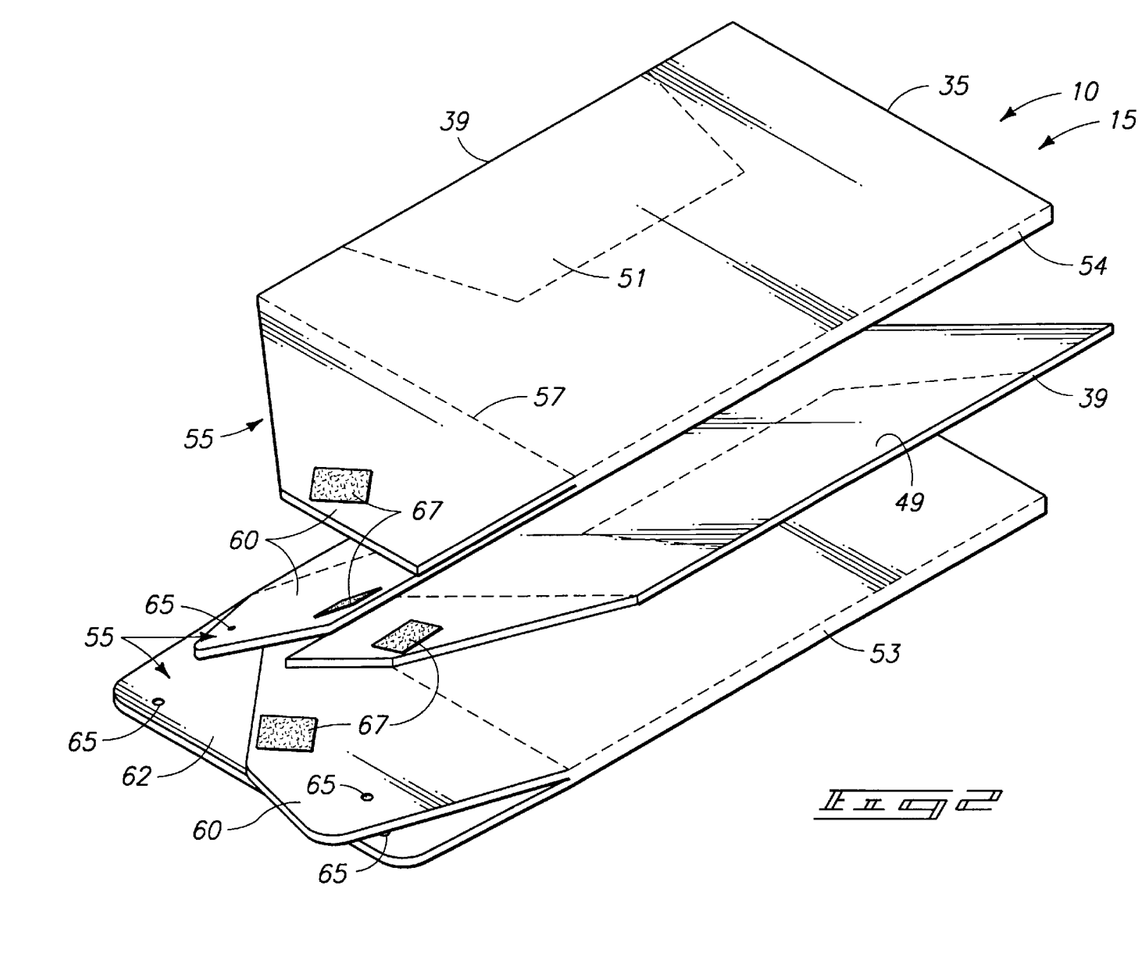
FIG. 2 is a perspective view of the first preferred form being folded toward a closed inoperative condition.
Figure 3:
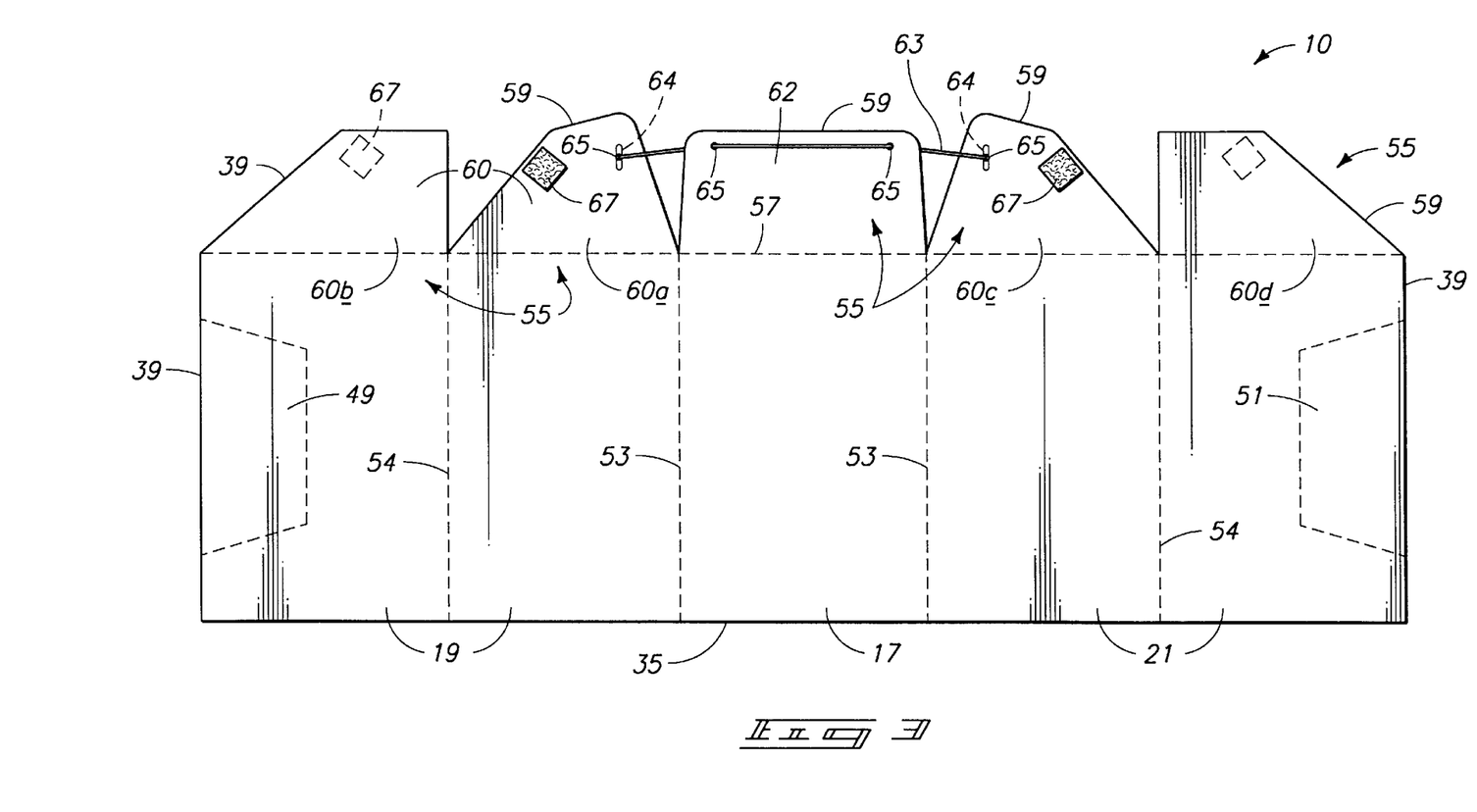
FIG. 3 is a flat pattern view of the first preferred form.

In the second preferred form, slits 66 are formed through the shield material from edges of the flange sections 60a–d to the holes 65. The slits 66 allow ends of the rubber band filament 63 to be secured to the flange sections 60a–d in the manner shown in FIGS. 6 and 9. Hole spacing in both preferred forms is arranged such that the elastic filament 63 will be in tension, either gently pulling the sides toward one another in the open condition (FIGS. 1 and 6) or yieldably holding the sides in the closed condition (FIGS. 2 and 7). To this end, the elastic filament 63 will stretch as the sides are folded toward either condition, and then act when the sides are released to pull one side toward the other with the central longitudinal fold lines 53 (adjoining the anterior surface 17) acting as fulcrums.

In the inoperative condition (FIGS. 2 and 7), the sides are folded above the anterior side 17 and the elastic filament 63 is situated above the fold lines 53 which act as fulcrums. In the operative condition (FIGS. 1 and 6), the sides are folded below the anterior side 17 and the elastic filament 63 is situated below the fold line 53 "fulcrums". The elastic filament 63 will pull the sides to the closed condition, and will pull the sides toward the open condition across the anterior flange section 62, depending upon the folded positions of the flange sections in relation to the folds 53.

In the first preferred form, the pairs of flange sections 60a–d are provided with patches 67 of hook and loop fastener material. The patches 67 interconnect in the operative condition to hold the flange sections 60a–d substantially coplanar, and to hold the edges 39 in their desired spaced relationship.

In operation of the first two preferred forms of the present invention, the user is aided in converting the shield between the inoperative and operative conditions by the elastic filament 63. To fold the shield from the inoperative condition to the operative condition, she simply grasps the support edges 39 and pulls them apart, while folding the sides downwardly with respect to the anterior surface 17. The filament 63 will stretch and move with the sides as they fold downwardly, automatically folding the anterior flange section 62 downwardly as well. She then simply holds the edges apart and fits the shield (now in the operative condition) over her head. The shield will now function to block the tanning radiation from the users face. When it is desired, the shield can be returned to the closed condition by again pulling the support edges 39 apart, but this time with an upward folding motion. As the sides fold to an elevation above the anterior surface 27, the elastic filament 63 will act to pull the sides together to the configuration shown in FIGS. 2 and 7.

Turning now to the alternate form of the invention, FIGS. 10–17 show double flange sections 70 that include outwardly projecting tabs 71. The sections 70 may be folded double along fold lines 58 to position the tabs 71 for engagement with complementary slots 73 (FIGS. 10, 11, 15 and 16) formed within appropriate surfaces 17, 19, or 21. The tabs 71 lock the flange sections 70 in their folded, operative positions to define the assembled flange 31.

Figures 12, 14:
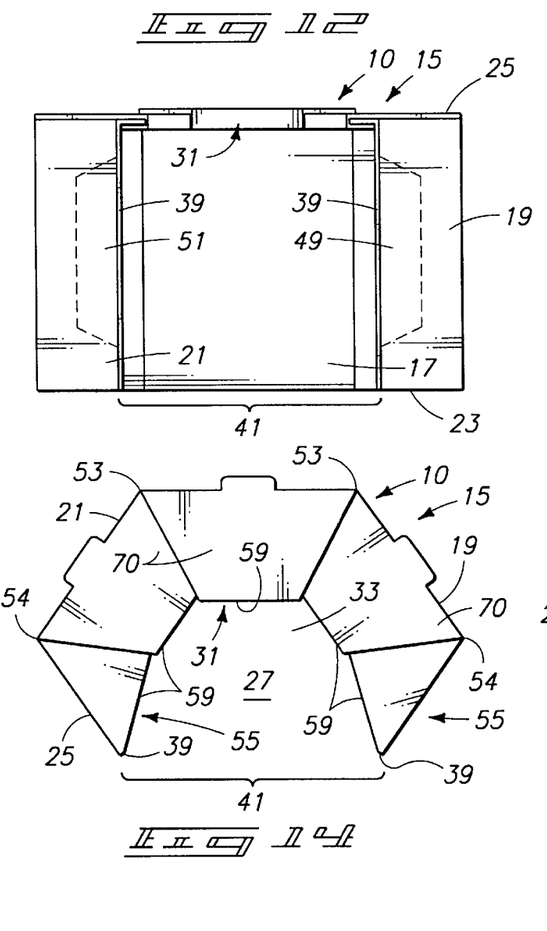
FIG. 12 is a posterior plan view of the FIG. 10 embodiment.
FIG. 14 is a inferior end view of the FIG. 10 embodiment.
Figure 13:
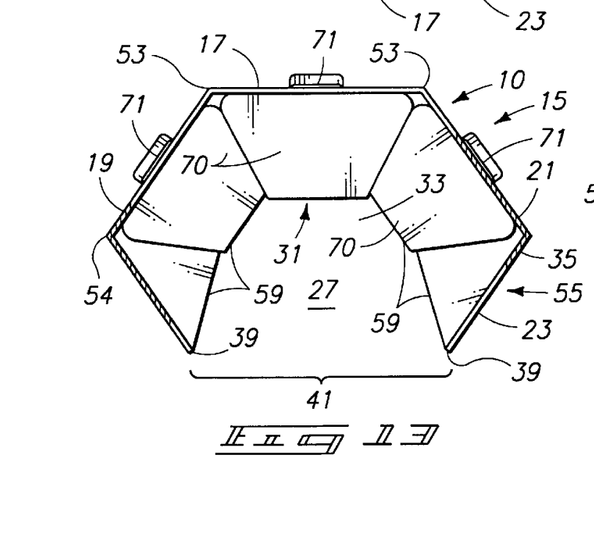
FIG. 13 is a superior end view of the FIG. 10 embodiment.
Figure 15:
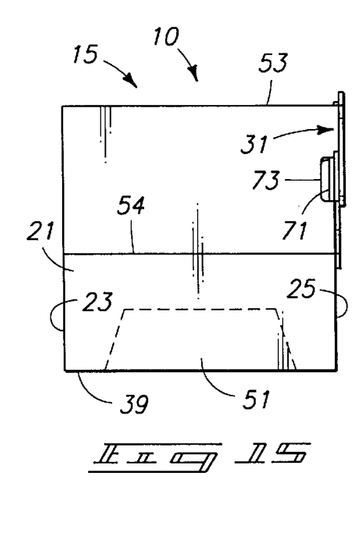
FIG. 15 is a side elevation view of the FIG. 10 embodiment.
Figure 16:
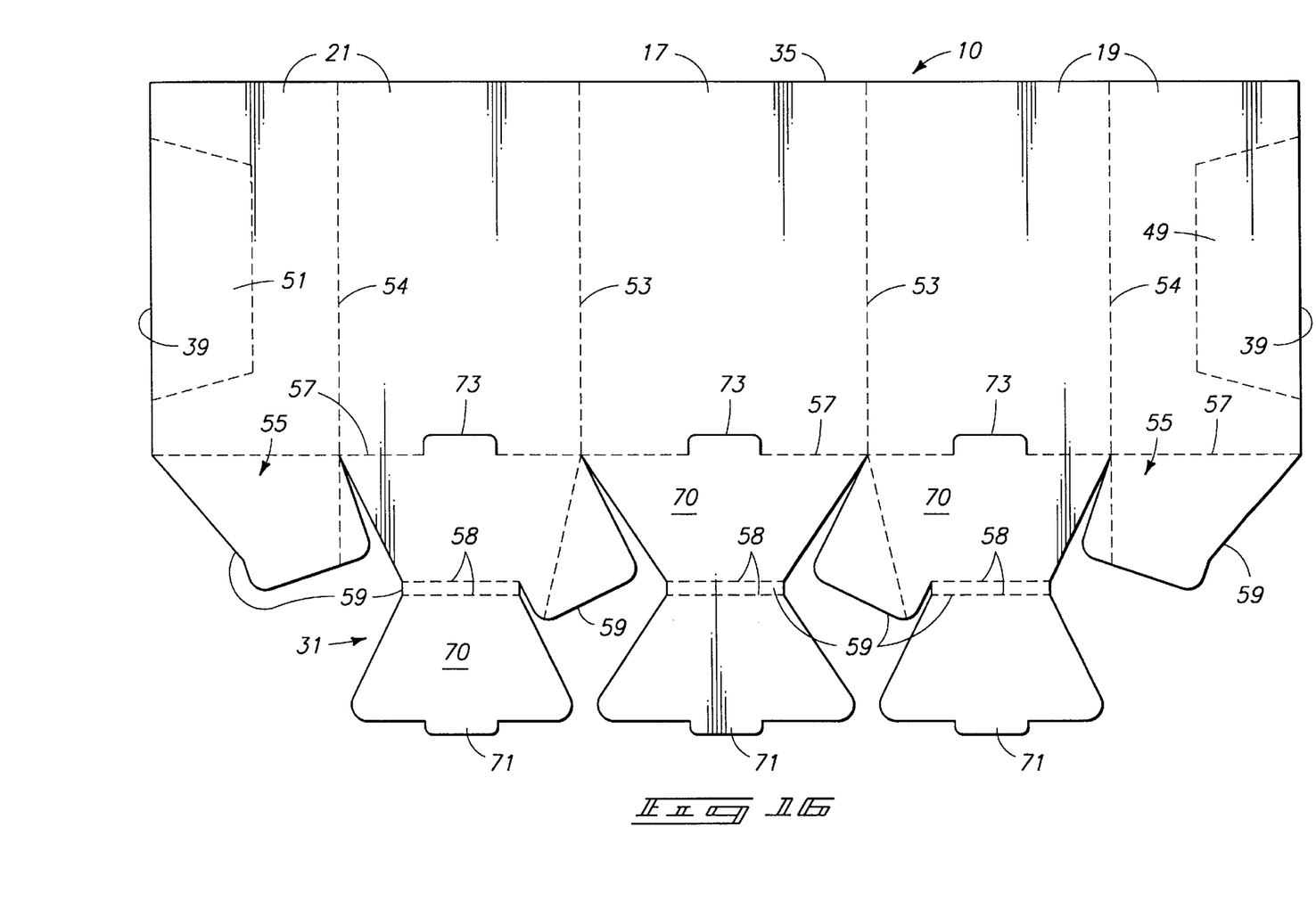
FIG. 16 is a flat pattern view of the FIG. 10 embodiment.
Figure 17:
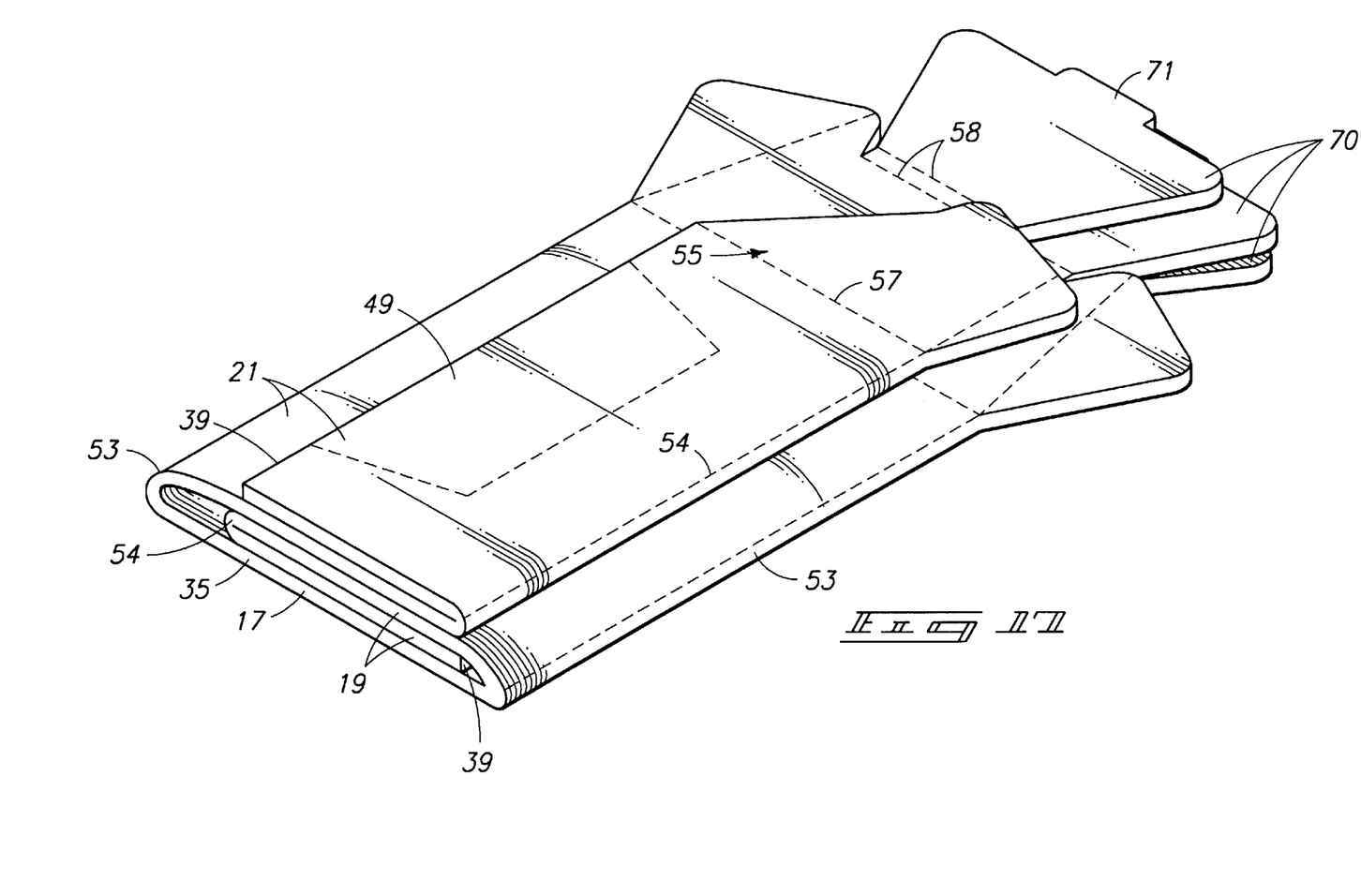
FIG. 17 is a view of the FIG. 10 embodiment folded to a storage configuration.

Use of the alternate form of shield is a simple matter of folding the sheet along the fold lines 53, 54 from the flat condition shown in FIG. 12 to initially form the compartment 27. Next all the flange sections are folded approximately 90° inwardly about the fold lines 57, 58. The tabs 71 of flange sections 70 are inserted in slots 73. All the flange sections interlock as shield is folded to the operative condition and is ready for use.

In using any form of the present shield, the user simply places the shield body over her head, such that the U-shaped recess 33 is adjacent the point of her chin. The axial support edges 39 will rest on the surface supporting the user's head.

If a tanning bed 11 is being used and the bed is provided with a pillow, the user may elect to remove the cut out sections 49, 51 and place the shield so the pillow is received within the cut out areas and the support edges 39 rest against the bed surface. The shield will now function to effectively prevent tanning rays from reaching the user's face.

Once the tanning session is complete, the user may unfold the shield by reversing the above folding process. The various fold lines may be used in the various forms at this time to enable the user to fold the shield to a flat, compact state for transport and storage. Any of several folded configurations may be selected according to the user's desire, or the shield can simply be left in the operative condition for future use.

It is pointed out that the preferred forms described above are independent of any tanning bed. In fact, if it is desired, the shield may be used outside to shade a user's face from direct sunlight, as when sun bathing.

It is also pointed out that the shield could be modified in form as exemplified in FIG. 18 to become adjustably attached to a tanning bed; specifically to the tanning bed lid and thus become a relatively permanent fixture of the bed itself. To this end the shield is mounted to the tanning bed by a bracket 80. In this form, the shield will remain in the open, operative condition and remain within the tanning bed for repeated use, and will move with the bed lid to cover and uncover the user's face. Construction of the shield in this form may be similar to that described above.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

I claim:

1. A tanning bed face shield, comprising:
   a light shielding body including an anterior surface and opposed side surfaces adjoining the anterior surface;
   wherein the anterior and side surfaces extend axially between a superior and an inferior end of said light shielding body;
   said surfaces forming a head receiving compartment sized to loosely receive and cover a user's face with an air space between the face and said surfaces;
   a flange assembly at the inferior end of the light shielding body, substantially normal to said surfaces and partially spanning the inferior end; and
   wherein the flange defines a substantially inverted U shaped recess configured to loosely receive a user's neck and overlap the chin to shield the inferior surface of the chin.

2. A face shield as claimed by claim 1, wherein the superior end includes lateral superior end surfaces defining a superior opening.

3. A face shield as claimed by claim 1, wherein the side surfaces terminate at spaced apart posterior support edges defining an axial head receiving opening adjoining the inverted U shaped recess.

4. A face shield as claimed by claim 1, further comprising lateral end edges on said surfaces defining the superior end and forming a cranial opening; and
   wherein the side surfaces terminate at spaced apart posterior support edges defining an axial head receiving opening adjoining the inverted U shaped recess and the superior opening.

5. A face shield as claimed by claim 1, wherein said surfaces and flange assembly are formed of a single sheet of foldable material.

6. A face shield as claimed by claim 1, wherein said surfaces and flange assembly are formed of a single sheet of opaque foldable material.

7. A face shield as claimed by claim 1, further comprising a cut out section on each of the opposed side surfaces for receiving a tanning bed pillow.

8. A face shield as claimed by claim 1, wherein the body is foldable between a relatively flat inoperative condition and an operative condition, and further comprising a biasing member connecting portions of the flange assembly to urge the flange assembly to the operative condition.

9. A tanning bed face shield, comprising:
   a sheet of foldable material;
   an anterior surface and side surfaces adjoining the anterior surface, defined along the sheet by longitudinal fold lines
   wherein the anterior and side surfaces extend axially between a superior end and a inferior end;
   said surfaces being foldable along said fold lines to form a head receiving compartment sized to loosely receive and cover a user's face with an air space between the face and said surfaces; and
   a flange assembly joined to the anterior and side surfaces along a flange fold line at the inferior end, foldable along the flange fold line to an operative condition partially spanning the head receiving compartment and forming a substantially inverted U shaped recess configured to loosely receive a user's chin and neck.

10. A face shield as claimed by claim 9, wherein said side surfaces terminate at longitudinal support edges that fold with the side surfaces to spaced positions forming a posterior opening across the head receiving compartment.

11. A face shield as claimed by claim 9, wherein said flange assembly is comprised of a plurality of flange sections joined to said surfaces at the flange fold line and wherein each flange section includes a flange edge surface that folds with the flange sections about the flange fold line to define an inverted U shaped recess configured to loosely receive a user's chin and neck.

12. A face shield as claimed by claim 9, wherein said flange assembly is comprised of a plurality of flange sections joined to said surfaces at the flange fold line and wherein each flange section includes a flange edge surface that folds with the flange sections about the flange fold line to define an inverted U shaped recess configured to loosely receive a user's chin and neck; and further comprising a biasing member interconnecting some of the flange sections to bias the flange sections to form the U shaped recess.

13. A face shield as claimed by claim 9, wherein said flange assembly is comprised of a plurality of flange sections joined to said surfaces at the flange fold line and wherein each flange section includes a flange edge surface that folds with the flange sections about the flange fold line to define an inverted U shaped recess configured to loosely receive a user's chin and neck; and wherein at least some of the flange sections include tabs that are foldable with the flange sections to engage slots formed within said surfaces.

14. A face shield as claimed by claim 9, wherein said side surfaces terminate at longitudinal edges that fold with the side surfaces to spaced positions forming an opening across the head receiving compartment, and further comprising cut-out sections leading into the side surfaces from the longitudinal side edges for receiving a tanning bed pillow.

15. A tanning bed face shield, comprising:

a light shielding body including an anterior surface and opposed side surfaces adjoining the anterior surface;

wherein the anterior and side surfaces extend axially between a superior and an inferior end of said light shielding body;

said surfaces forming a head receiving compartment sized to loosely receive and cover a user's face with an air space between the face and said surfaces; and wherein the head receiving compartment is open at the superior and inferior ends; and a flange assembly at the inferior end of the light shielding body, formed along a plane substantially normal to said surfaces and partially spanning the head receiving compartment at the inferior end and configured to loosely receive the user's neck and overlap the chin to shield the chin from light.

16. A tanning bed and face shield, comprising:

a tanning bed including a lid;

a face shield secured to the lid;

wherein the face shield includes a light shielding body with an anterior surface and opposed side surfaces adjoining the anterior surface;

wherein the anterior and side surfaces extend axially between a superior and a inferior end of said light shielding body and include spaced axial edges at a posterior side;

said axial edges forming a head receiving opening in open communication with a compartment defined by the anterior and side surfaces sized to loosely receive and cover a user's face with an air space between the face and said surfaces; and a flange at the inferior end of the light shielding body, formed along a plane substantially normal to said surfaces and partially spanning the head receiving compartment at the inferior end and configured to loosely receive the user's neck and overlap the chin to shield the chin from light.

\* \* \* \* \*